US005736335A

United States Patent [19]
Emmons et al.

[11] Patent Number: 5,736,335
[45] Date of Patent: *Apr. 7, 1998

[54] DRY ELEMENTS, TEST DEVICES, TEST KITS AND METHODS FOR CHEMILUMINESCENT DETECTION OF ANALYTES USING PEROXIDASE-LABELED REAGENTS

[75] Inventors: Robert Edwin Emmons, Victor; John Charles Mauck, Rochester, both of N.Y.; Paul James Heaney, Branford; Dietmar Karl Freund, Glendale, both of Conn.; David Brewer LaTart, Rochester, N.Y.; Richard George Chubet, Middletown; Douglas Lincoln Vizard, Cheshire, both of Conn.

[73] Assignee: Eastman Kodak Company, Rochester, N.Y.

[ * ] Notice: The term of this patent shall not extend beyond the expiration date of Pat. No. 5,641,635.

[21] Appl. No.: 783,049

[22] Filed: Jan. 14, 1997

Related U.S. Application Data

[63] Continuation of Ser. No. 589,129, Jan. 22, 1996, Pat. No. 5,641,635, which is a continuation of Ser. No. 153,141, Nov. 12, 1993, abandoned.

[51] Int. Cl.$^6$ ........................................ C12Q 1/68
[52] U.S. Cl. .............. 435/6; 435/7.91; 435/7.92; 435/28; 435/962; 435/968; 435/970; 435/975; 436/169; 436/170; 436/172; 422/52; 422/68.1

[58] Field of Search .................. 435/6, 7.91, 7.92, 435/28, 962, 968, 970, 975; 436/169, 170, 172; 422/52, 68.1

[56] References Cited

U.S. PATENT DOCUMENTS

| 4,231,754 | 11/1980 | Vogelhut ......................... 436/172 |
| 4,808,529 | 2/1989 | Doppelfield et al. ............ 435/179 |
| 5,047,322 | 9/1991 | Emmons et al. .................. 435/6 |
| 5,239,406 | 8/1993 | Coffman et al. ................. 428/232 |
| 5,279,940 | 1/1994 | Kissel .............................. 435/6 |

FOREIGN PATENT DOCUMENTS

| 0230762 | 8/1987 | European Pat. Off. . |
| 0331077 | 9/1989 | European Pat. Off. . |
| 62-103542 | 7/1992 | Japan . |
| 2246197 | 1/1992 | United Kingdom . |

*Primary Examiner*—Lora M. Green
*Attorney, Agent, or Firm*—J. Lanny Tucker

[57] ABSTRACT

A dry, removable analytical element can be used to detect chemiluminescent signals produced from the reaction of peroxidase and a chemiluminescent detection system. The analytical element contains at least two layers, the outer layer being non-tacky and water-soluble or water-permeable, and used to contact a gel plate or transblotting membrane in which multiple analytes are located. The resulting signal can be recorded using a photosensitive element. Test kits include the various packaged components needed to use the analytical element for analyte detection. Within the element are critical amounts of oxidase and an oxidase substrate for highly sensitive analyte detection.

14 Claims, No Drawings

DRY ELEMENTS, TEST DEVICES, TEST KITS AND METHODS FOR CHEMILUMINESCENT DETECTION OF ANALYTES USING PEROXIDASE-LABELED REAGENTS

RELATED APPLICATION

This application is a continuation of U.S. Ser. No. 08/589,129 filed Jan. 22, 1996, now U.S. Pat. No. 5,641,635, which was a continuation of U.S. Ser. No. 08/153,141, filed Nov. 12, 1993, now abandoned.

FIELD OF THE INVENTION

This invention relates to the determination of analytes using dry, removable analytical elements and test kits for clinical analysis, or biological or biomedical research. In particular, it relates to dry, removable analytical elements, test devices, test kits and methods for detecting peroxidase-labeled analytes using chemiluminescent reagent systems.

BACKGROUND OF THE INVENTION

A variety of analytical procedures have been developed for the separation and identification of different molecular species present in a specimen. Separation is generally accomplished by applying the specimen to a water-containing solid medium and inducing molecular separation of the species within the medium. In particular, chromatography and electrophoresis have been employed, both of which provide separation of different molecular species. The separation medium is often called a chromatographic medium or electrophoretic plate. In such processes, a variety of reagents which interact with one or more analytes in the specimen may also be applied to the medium before, during or after the separation process to assist in separation or identification of the analytes.

The detection of analytes with labeled reagents (such as labeled probes or antibodies) is a commonly used method in research and clinical laboratories. Various labels have been used, including magnetic particles, radioisotopes and enzymes, with horseradish peroxidase being one of the most common labels. Transparent, removable elements useful for producing a colorimetric signal in response to multiple analytes labeled with peroxidase are described in U.S. Pat. No. 5,047,322 (Emmons et al) and are available from international Biotechnologies, Inc. as ENZYGRAPHIC™ WEB.

While these elements have provided considerable advantages over the use of radioisotopes or magnetic particles as labels, there is a need for further improvement in sensitivity and a means to provide a permanent record of generated signal. The use of colorimetric signals may be suitable for immediate evaluation, but dyes tend to fade and prohibit the formation of a relatively permanent record.

It is believed that chemiluminescent assay systems would provide increased sensitivity, but current systems have several disadvantages. They require the use of wet chemistry reagents to promote the enzymatic reaction. Wet chemistry may also require dilutions of reagents, thereby reducing the sensitivity of the assay, and the handling of potentially hazardous chemicals.

U.S. Pat. No. 4,231,754 (Vogelhut) describes chemiluminescent analytical devices having multiple reagent layers which are separated from each other, for example, to form a pH gradient between layers. This is done because certain reagents are stable at relatively lower pH while a pH above 8 is desirable for effective production of chemiluminescent signal. Keeping layers at different pH values is very difficult when fluid samples or wet blot membranes are applied to the device unless immobilized buffers are used. However, having such immobilized reagents limits the usefulness of the device because only certain binders could be used in the devices. It is not believed that the devices described in this patent are practical.

More recently, U.S. Pat. No. 4,808,529 (Doppelfeld et al) describes test devices having enzymes attached directly to porous membranes having appropriate reactive groups. The signal is transferred to a transblotting membrane rather than the reaction taking place in the test device itself.

It was considered that a dry analytical element should be designed to provide chemiluminescent signals from multiple analytes. It would also be desired that such signals could be recorded in a permanent fashion since the signals do not last very long. Moreover, it would be desirable to have non-tacky, removable elements which would generate chemiluminescent signals in response to peroxidase labeled gel plates or transblotting membranes which allow the labeled plates or membranes to be used more than once. By "non-tacky" is meant that the element will not adhere to a gel plate or transblotting membrane, and can therefore be easily removed without damage to the gel plate or transblotting membrane.

It would also be desirable to have an element which has stable reagents for long term storage, is easy for the consumer to use and requires no reagent formulation.

SUMMARY OF THE INVENTION

The problems noted above have been solved with a dry, removable analytical element for producing a chemiluminescent signal in response to the catalytic action of a peroxidase, the element comprising a transparent, non-porous support having disposed thereon, in order:

one or more reagent layers buffered to a pH of from about 7.5 to about 11 and containing one or more hydrophilic binders, and a non-tacky, water-soluble or water-permeable cover layer, the element further comprising:
  (a) a chemiluminescent composition,
  (b) an enhancer for the chemiluminescent composition,
  (c) a micelle forming material for the chemiluminescent composition,
  (d) from about 300 to about 40,000 I.U./m$^2$ of an oxidase, and
  (e) at least about 1 g/m$^2$ of a substrate for the oxidase, the components (a)–(e) being located in any of the layers provided that the oxidase and the oxidase substrate are in separate layers.

A preferred embodiment is a dry, removable analytical element for producing a chemiluminescent signal in response to the catalytic action of a peroxidase, the element comprising a transparent, nonporous support having disposed thereon, in order:

a reagent layer comprising a chemiluminescent composition, an enhancer for the chemiluminescent composition, a micelle forming material for the chemiluminescent composition, a buffer providing a pH of from about 7.5 to about 11, and from about 300 to about 40,000 I.U./m$^2$ of an oxidase, all disposed in a hydrophilic binder, and a non-tacky, water-soluble or water-permeable cover layer comprising from about 1 to about 20 g/m$^2$ of a substrate for the oxidase dispersed in from about 0.2 to about 5.5 g/m$^2$ of a water-soluble or water-permeable film-forming polymer.

This invention also provides a test device comprising:

a) any of the dry, removable analytical elements described above, and b) a photosensitive element adapted to receive the chemiluminescent signal generated in the analytical element the photosensitive element being physically associated with the analytical element.

Further, this invention provides a method for determining one or more analytes, the method comprising the steps of:

A) forming a temporary laminate by overlaying a gel plate or transblotting membrane containing one or more analytes labeled with peroxidase with any of the dry, removable analytical elements described above, to generate a chemiluminescent signal in the analytical element in response to the peroxidase-labeled analytes in the gel plate or transblotting membrane, and B) detecting the generated chemiluminescent signal as a means of detecting the one or more analytes.

Moreover, a method for recording the determination of one or more analytes comprises the steps of:

A) forming a temporary laminate by overlaying a gel plate or transblotting membrane containing one or more analytes labeled with a peroxidase with any of the dry, removable analytical elements described above, to generate a chemiluminescent signal in the analytical element in response to peroxidase-labeled analytes in the gel plate or transblotting membrane, B) exposing a photosensitive element to the chemiluminescent signal generated in the dry analytical element to form a latent image, and C) generating a permanent record of the chemiluminescent signal from the latent image of the exposed photosensitive element.

Further, a test kit for the determination of one or more analytes comprises:

a) any of the dry, removable analytical elements described above, and b) one or more separately packaged components selected from the group consisting of:

i) a buffered salt solution comprising tris (hydroxymethyl)aminomethane and an inorganic salt, ii) a buffered blocking solution comprising from about 0.5 to about 5 weight % of casein, iii) a peroxidase-labeled specific binding reagent, iv) an oligonucleotide labeled directly or indirectly with a peroxidase, v) a transblotting membrane, vi) a gel plate, and vii) a photosensitive element.

The present invention provides a highly sensitive means for detecting a plurality of analytes, particularly analytes which have been separated using gel plates or other separation means, or which have been immobilized in a transblotting membrane. The analytical element can be readily removed from such plates or membranes which tend to be tacky when wet, and chemiluminescent signals generated thereby can be permanently recorded using suitable photosensitive elements. The bands on an electrophoretic plate are well defined with the element of this invention compared to other known enzyme detection systems.

However, the invention is not limited to such means of detection since the analytical element can be used to detect analytes in a fluid specimen, as well as those immobilized on conventional supports such as gel plates and transblotting membranes. The method is relatively inexpensive, easy to use, highly sensitive and avoids solutions of reagents. The results can be qualitative or quantitative. Because the tested specimen is not stained with this method, multiple analyte probes can be used if desired. Since the element is non-tacky and can be peeled off a membrane or gel plate, the membrane or gel plate can be used more than once using additional analytical elements or different detection means. The element reagents are stable when stored for lengthy times at cold temperatures, and the element is ready to use without preparation or activation.

The analytical element of this invention provides these advantages because of the non-tacky, removable cover layer comprising one or more water-soluble or water-permeable materials. Particularly useful are water-soluble or water-permeable film forming polymers such as vinylpyrrolidone polymers. The high sensitivity is achieved using specific levels of oxidase and oxidase substrate. Moreover, the test kits contain useful buffered and blocking solutions which reduce background when peroxidase-labeled reactants are detected in gel plates or transblotting membranes.

DETAILED DESCRIPTION OF THE INVENTION

The present invention can be used to advantage in various fields of endeavor including medicine, immunology, molecular biology, biochemistry, clinical chemistry and others too numerous to mention. Proteins, nucleic acids, intact cells (or components thereof) and other biological analytes which can be labeled directly or indirectly by a peroxidase can be determined using the present invention. In addition, the invention can be used to determine a peroxidative substance such as a peroxidase. As used herein, "determination" is intended to mean qualitative, quantitative or semi-quantitative detection of the analytes of interest.

In particular, the invention is useful to detect proteins or nucleic acids which have been electrically induced to migrate through an aqueous medium and be separated from each other on the basis of molecular charge. Moreover, it is also useful to detect proteins or nucleic acids which have been induced to migrate through a hydrophilic medium and be separated from each other on the basis of molecular weight, isoelectric point or both. Other uses of the invention would become readily apparent to one skilled in the art in view of the teaching herein.

The use of the analytical element is quite simple because of the diffusibility of the various reagents which produce a chemiluminescent signal. When the cover layer of the element is placed in contact with a wetted gel plate or transblotting membrane, diffusion of reagents and chemical and enzymatic reactions occur. The oxidase or its substrate diffuse within the element until they encounter each other, and react to produce hydrogen peroxide. This oxidant and the enhancer diffuse out of the element into the gel plate or membrane where the peroxidase label on the analytes catalyzes the dissociation of the hydrogen peroxide. The active oxygen from the peroxide reacts with the chemiluminescent composition (for example, luminol) in the presence of the enhancer to generate an emission of light. The location and level of this signal can be recorded as a measure of the presence or amount of the labeled analytes. Because all of these critical reactions are needed, it is important that the oxidase substrate and enhancer are very mobile within the element.

In the context of this application, "proteins" include peptides, polypeptides, enzymes, lipoproteins, glycoproteins, and other proteins, as well as fragments or genetically engineered constructs thereof (such as Fab, Fab', Fab$_2$', Fc and what are known as single-chain constructs). By "nucleic acids" is meant both single- and double-chain nucleic acids and components thereof, and both naturally occurring and synthetic oligonucleotides having at least four nucleotides.

A plurality of such analytes is usually present in a biological specimen to be tested. In general, in one embodiment of this invention, such a specimen is contacted with an electrophoretic or electrofocusing plate where the analytes are induced to migrate electrically using known procedures, reagents and buffered solutions. Once separated in the plate, the analytes can be labeled directly or indirectly with a peroxidase (described below) and then detected by laminating the element of this invention with the plate to generate a chemiluminescent signal. Such signal can also be recorded by means of a suitable photosensitive layer or element which is exposed to the chemiluminescent signal in a suitable manner such that the chemiluminescent signal causes the formation of latent images in the photosensitive layer or element. For example, the photosensitive element can be placed in contact with the element of this invention, or merely placed in proximity in a suitable cassette which protects the photosensitive element from ambient light. In another embodiment, the chemiluminescent signal can be recorded with a camera or other optical device containing a suitable photographic film.

Useful electrophoretic or electrofocusing plates are well known and a number of them are commercially available from several sources. Others are described in U.S. Pat. No. 3,975,162 (Renn) and U.S. Pat. No. 5,047,322 (Emmons et al). Particularly useful gel plates have thin layers of hydrated gels, such as agarose, agar, polyacrylamide, cellulose acetate and other materials known in the art, and usually have one or more compartments. Plates composed of agarose and polyacrylamide are preferred in the practice of this invention.

In another embodiment, the specimen can be applied or transferred to a transblotting membrane which are useful in Western, Southern, Northern, slot, thermal, lift and dot blotting techniques which are well known in the art. Such membranes are commercially available from a number of sources, and are prepared from such materials as nitrocellulose, polyamides (for example, nylon-66) and cellulose acetate. Nitrocellulose or nylon-66 membranes are preferred. As described above, the separated analytes can be appropriately labeled with a peroxidase and detected by laminating the analytical element of this invention with the transblotting membrane. The chemiluminescent signal thus generated can also be recorded as described herein.

The element of this invention has a transparent, nonporous support upon which the layers are disposed using suitable techniques (such as by coating). By "transparent" is meant that the supports are transmissive of chemiluminescent signals. They are generally prepared from transparent formulations of polymeric materials such as cellulose acetate, poly(ethylene terephthalate), a polycarbonate or a polyvinyl material such as polystyrene. Other materials would be readily apparent to one skilled in the art. Transparent subbing layers of conventional materials may be applied to the support to improve adhesion of other layers.

In one or more layers (such as a reagent layer or the cover layer), is a chemiluminescent composition which is capable of producing a chemiluminescent signal in response to reaction of an oxidant, such as hydrogen peroxide, urea peroxide or sodium perborate, in the presence of a peroxidase. The chemiluminescent composition can be a single reagent compound or a combination of reagent compounds which produce the desired signal. In most assays, hydrogen peroxide is generated from the reaction of an oxidase with its substrate. Such oxidase-substrate pairs include glucose oxidase-glucose, sarcosine oxidase-sarcosine, cholesterol oxidase-cholesterol, D-galactose oxidase-D-galactose and L-glycerol-3-phosphate oxidase-L-glycerol-3-phosphate. Preferably, glucose and glucose oxidase are used in the element of this invention.

Useful chemiluminescent compositions, include but are not limited to, tetrabis(dimethylamino)ethylene, luciferin, lucigenin and oxalyl chloride.

Particularly useful compositions for generating chemiluminescent signals comprise a 2,3-dihydro-1,4-phthalazinedione (identified herein as a "DPD"). Any free or conjugated 2,3-dihydro-1,4-phthalazinedione that can be converted to an excited state in a chemiluminescent reaction and then returns to a non-excited state with the emission of light, is useful in the practice of this invention. A considerable number of such compounds are known in the art, including those described in U.S. Pat. No. 4,598,044 (Kricka et al) and *Chemiluminescence in Organic Chemistry*, Gundermann and McCapra, Springer-Verlag, Berlin, 1987, pages 204–207. Such compounds are generally known as "luminol type hydrazides" and include phthalic hydrazides, naphthalene-1,2-dicarboxylic acid hydrazides, anthracene-2,3-dicarboxylic acid hydrazides, phenathrene-1,2-dicarboxylic acid hydrazides, fluorene-1,2-dicarboxylic acid hydrazides, benzo[g,h,i]perylene-1,2-dicarboxylic acid hydrazides, coronene-1,2-dicarboxylic acid hydrazides, and others readily apparent to one skilled in the art.

In particular, the DPD is defined by the structure (V):

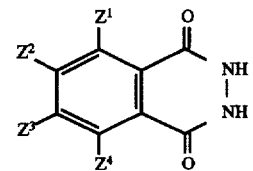

wherein $Z^1$, $Z^2$, $Z^3$ and $Z^4$ are independently hydrogen, alkyl of 1 to 6 carbon atoms (such as methyl, ethyl, isopropyl, t-butyl, sec-pentyl and hexyl), alkenyl of 2 to 6 carbon atoms [such as ethenyl, 1-propenyl, isobutenyl, 2-(N,N-diisopropylamino)vinyl, 2-(N,N-diisobutylamino)vinyl, 2-(N,N-diisopentylamino)vinyl and 2-hexenyl], hydroxy, alkoxy of 1 to 6 carbon atoms (such as methoxy, ethoxy, isopropoxy, t-butoxy and hexoxy), carboxy, amino [including amino substituted with alkyl or alkanoyl, such as methylamino, ethylamino, amido (for example, acetamido and hexanamido), dimethylamino, diethylamino and diisobutylamino], conjugated aminoalkenyl (for example, as defined below) or aminoaryl [including substituted aminoaryl, such as p-(N,N-dimethylamino)phenyl, p-(N,N-diethylamino)phenyl and 5-amino-2,3-dihydro-1,4-phthalazinedion-8-yl (also known as luminyl)].

At least one of $Z^1$ and $Z^2$ is amino (including substituted amino, as defined above), conjugated aminoalkenyl (including substituted aminoalkenyl as described above) or aminoaryl [such as p-(N,N-dimethylamino)phenyl, p-(N,N-diethylamino)phenyl and 5-amino-2,3-dihydro-1,4-phthalazinedion-8-yl]. As used herein, "conjugated aminoalkenyl" refers to a monovalent group capable of electron resonance from the amino group through the alkenyl group to the aromatic ring of the phthalazinedione where it is substituted, and includes for example, a dialkylaminovinyl group [such as 2-(N,N-diisopropylamino)vinyl, 2-(N,N-diisobutylamino)vinyl and 2-(N,N-diisopentylamino)vinyl], and dialkylaminobutadienyl groups, such as 4-(N,N-diethylamino)-1,3-butadien-1-yl.

Alternatively, any adjacent two, adjacent three or all of $Z^1$, $Z^2$, $Z^3$ and $Z^4$ (that is, combinations of two or three adjacent groups, or all four groups) can be taken together to form a fused ring system containing one or more aromatic rings. Such fused rings can be substituted with one or more hydroxy, amino (substituted or unsubstituted as described above) or alkoxy of 1 to 4 carbon atoms (such as methoxy, ethoxy and isopropoxy). Preferably, such fused rings are substituted with one or more primary, secondary or tertiary amines, hydroxy or alkoxy as described above.

Representative useful DPD compounds include, but are not limited to, luminol, isoluminol, N-(4-aminobutyl)-N-ethylisoluminol hemisuccinimide, N-(6-aminohexyl)-N-ethylisoluminol, N-ethylisoluminol and 7-dimethylaminonaphthalene-1,2-dicarboxylic acid hydrazide. Luminol(5-amino-2,3-dihydro-1,4-phthalazinedione) and isoluminol(6-amino-2,3-dihydro-1,4-phthalazinedione) are preferred, and luminol is most preferred.

Other useful classes of DPD compounds are described in the Gundermann and McCapra publication noted above, and include substituted or unsubstituted phthalic acid hydrazides, anthracene-2,3-dicarboxylic acid hydrazides, phenathrene dicarboxylic acid hydrazides, fluorene-1,2-dicarboxylic acid hydrazides, benzo[g,h,i]perylene-1,2-dicarboxylic acid hydrazides and coronene-1,2-dicarboxylic acid hydrazides, such as those illustrated by the following structures:

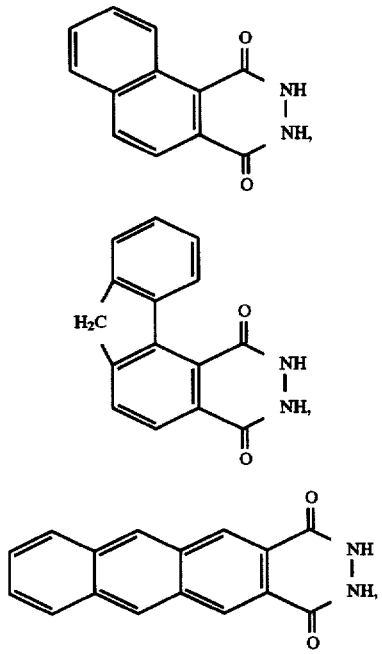

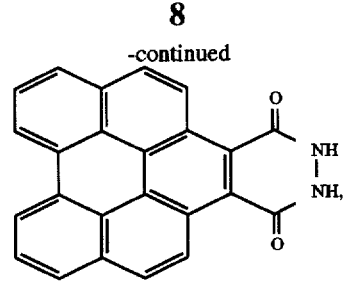

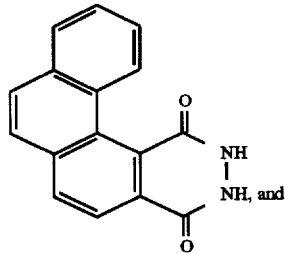

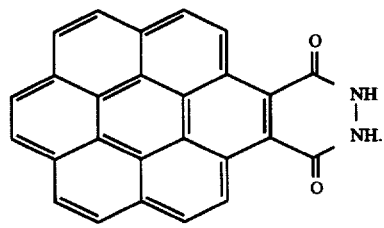

The DPD compounds noted above can be obtained commercially, or be prepared using conventional starting materials and known procedures.

Compounds which enhance the generation of a chemiluminescent signal are known as "enhancers" which are believed to act as electron transfer agents. Any of those known for such purposes can be used in the practice of this invention. Mixtures can also be used. Particularly useful enhancers are described, for example, in U.S. Pat. No. 4,598,044 (Kricka et al), U.S. Pat. No. 4,729,950 (Kricka et al) and U.S. Pat. No. 4,828,983 (McClune), incorporated herein by reference, and include such compounds as p-iodophenol, 1,6-dibromonaphth-2-ol, 1-bromonaphth-2-ol, 6-hydroxybenzothiazole, 2,4-dichlorophenol, p-hydroxycinnamic acid, dehydroluciferin, N,N,N'N'-tetramethylbenzidine, p-bromophenol, p-chlorophenol.

Also useful as enhancers are compounds having any of structures (I):

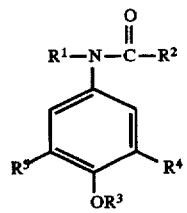

(II):

-continued

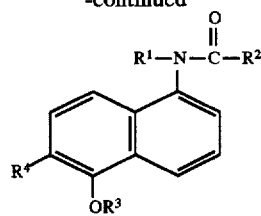

(III):

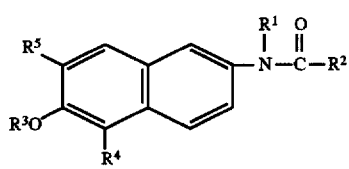

or (IV):

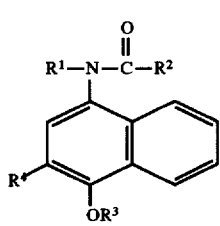

wherein $R^1$ is hydrogen or alkyl of 1 to 4 carbon atoms (such as methyl, ethyl, isopropyl, hydroxymethyl, aminomethyl and methoxymethyl). Preferably, $R^1$ is hydrogen.

In structure (I), (II), (III) and (IV), $R^2$ is hydrogen, alkyl of 1 to 4 carbon atoms (such as methyl, ethyl, isopropyl, t-butyl and isobutyl), alkoxyalkyl of 1 to 4 carbon atoms (such as methoxymethyl and methoxyethyl), hydroxyalkyl of 1 to carbon atoms (such as hydroxymethyl, 1-hydroxyethyl, 2-hydroxyethyl and 2,3-dihydroxypropyl), aminoalkyl of 1 to 4 carbon atoms (such as aminomethyl, 2-aminoethyl, 3-aminopropyl, 2,4-diaminobutyl, methylaminomethyl, 2,2-dimethylaminoethyl and 4-aminobutyl), haloalkyl of 1 to 4 carbon atoms (such as chloromethyl, bromomethyl, 2-chloroethyl, 1,1-dichloroethyl, 1,1,1-trichloromethyl, 2,2,2-trichloroethyl and 3-chloropropyl), or alkenyl of 2 to 5 carbon atoms (such as ethenyl, 1-propenyl, isopropenyl and 2-butenyl). Preferably, $R^2$ is hydrogen, methyl or ethenyl.

$R^3$ is hydrogen or alkyl of 1 to 4 carbon atoms (such as methyl, ethyl, isopropyl, t-butyl, n-butyl and isobutyl). Preferably, $R^3$ is hydrogen or methyl.

$R^4$ and $R^5$ are independently hydrogen or an electron withdrawing group having a Hammett sigma value of at least about 0.01, and preferably at least about 0.3. Hammett sigma values are calculated in accordance with standard procedures described, for example, in *Steric Effects in Organic Chemistry*, John Wiley & Sons, Inc., 1956, pp. 570–574 and *Progress in Physical Organic Chemistry*, Vol. 2, Interscience Publishers, 1964, pp. 333–339. Representative electron withdrawing groups having positive Hammett sigma values include cyano, carboxy, nitro, halo (fluoro, bromo, chloro or iodo), trihalomethyl (for example, trifluoromethyl or trichloromethyl), carbonyl, carbamoyl, sulfonyl, sulfamoyl, esters, and others readily apparent to one skilled in the art. Preferred electron withdrawing groups are halo (such as chloro or bromo) and cyano. Chloro and cyano are more preferred electron withdrawing groups, and chloro is most preferred for either of $R^4$ and $R^5$.

In the foregoing structure (I), preferably at least one of $R^4$ and $R^5$ is an electron withdrawing group as defined above.

Representative enhancers having structure include:
3'-chloro-4'-hydroxyacetanilide,
3',5'-dichloro-4'-hydroxyacetanilide,
3'-fluoro-4'-hydroxyacetanilide,
3',5'-difluoro-4'-hydroxyacetanilide,
3'-bromo-4'-hydroxyacetanilide,
3',5'-dibromo-4'-hydroxyacetanilide,
3'-cyano-4'-hydroxyacetanilide,
3',5'-dicyano-4'-hydroxyacetanilide,
N-methyl-N-(3-chloro-4-hydroxyphenyl)acetamide,
N-(3-chloro-4-hydroxyphenyl)methacrylamide,
N-(3-chloro-4-methoxyphenyl)acetamide,
N-(3-chloro-4-hydroxyphenyl)-2-chloroacetamide,
N-(3-chloro-4-hydroxyphenyl)-2,2-dichloroacetamide,
N-(3-chloro-4-hydroxyphenyl)-2,2,2-trichloroacetamide,
N-(3-chloro-4-hydroxyphenyl)-2-hydroxyacetamide,
N-(3-chloro-4-hydroxyphenyl)-2-methoxyacetamide, and
N-(3-chloro-4-hydroxyphenyl)-2-aminoacetamide.

Representative enhancers of structure (II) include:
N-(5-hydroxy-1-naphthyl)acetamide,
N-(5-hydroxy-6-fluoro-1-naphthyl)acetamide,
N-(5-hydroxy-6-chloro-1-naphthyl)acetamide,
N-(5-hydroxy-6-cyano-1-naphthyl)acetamide,
N-methyl-N-(5-hydroxy-1-naphthyl)acetamide,
N-methyl-N-(5-hydroxy-6-chloro-1-naphthyl)acetamide,
N-(5-methoxy-1-naphthyl)acetamide,
N-(5-methoxy-6-chloro-1-naphthyl)acetamide,
N-(5-hydroxy-1-naphthyl)-2-chloroacetamide,
N-(5-hydroxy-1-naphthyl)-2,2-dichloroacetamide,
N-(5-hydroxy-6-chloro-1-naphthyl)-2,2-dichloroacetamide,
N-(5-hydroxy-1-naphthyl)-2,2,2-trichloroacetamide,
N-(5-hydroxy-6-chloro-1-naphthyl)-2,2,2-trichloroacetamide,
N-(5-hydroxy-1-naphthyl)-2-hydroxyacetamide,
N-(5-hydroxy-6-chloro-1-naphthyl)-2-hydroxyacetamide,
N-(5-hydroxy-1-naphthyl)-2-methoxyacetamide,
N-(5-hydroxy-6-chloro-1-naphthyl)-2-methoxyacetamide,
N-(5-hydroxy-1-naphthyl)-2-aminoacetamide, and
N-(5-hydroxy-6-chloro-1-naphthyl)-2-aminoacetamide.

Representative enhancers of structure (III) include:
N-(6-hydroxy-2-naphthyl)acetamide,
N-(6-hydroxy-5-fluoro-2-naphthyl)acetamide,
N-(6-hydroxy-7-fluoro-2-naphthyl)acetamide,
N-(6-hydroxy-5,7-difluoro-2-naphthyl)acetamide,
N-(6-hydroxy-5-chloro-2-naphthyl)acetamide,
N-(6-hydroxy-5,7-dichloro-2-naphthyl)acetamide,
N-(6-hydroxy-7-bromo-2-naphthyl)acetamide,
N-(6-hydroxy-5,7-dibromo-2-naphthyl)acetamide,
N-(6-hydroxy-5-cyano-2-naphthyl)acetamide,
N-(6-hydroxy-5,7-dicyano-2-naphthyl)acetamide,
N-methyl-N-(6-hydroxy-5-chloro-2-naphthyl)acetamide,
N-methyl-N-(6-hydroxy-7-chloro-2-naphthyl)acetamide,
N-methyl-N-(6-hydroxy-5,7-dichloro-2-naphthyl)acetamide,
N-(6-methoxy-2-naphthyl)acetamide,
N-(6-methoxy-5-chloro-2-naphthyl)acetamide,
N-(6-methoxy-5,7-dichloro-2-naphthyl)acetamide,
N-(6-hydroxy-2-naphthyl)-2-chloroacetamide,
N-(6-hydroxy-7-chloro-2-naphthyl)-2-chloroacetamide,
N-(6-hydroxy-2-naphthyl)-2,2-dichloroacetamide,
N-(6-hydroxy-7-chloro-2-naphthyl)-2,2,2-trichloroacetamide,
N-(6-hydroxy-2-naphthyl)-2-hydroxyacetamide,
N-(6-hydroxy-5-chloro-2-naphthyl)-2-methoxyacetamide, N-(6-hydroxy-2-naphthyl)-2-aminoacetamide, and
N-(6-hydroxy-5,7-dichloro-2-naphthyl)-1-aminoacetamide.

Representative compounds of structure (IV) include:
N-(4-hydroxy-1-naphthyl)acetamide,
N-(4-hydroxy-5-chloro-1-naphthyl)acetamide,
N-methyl-N-(4-hydroxy-3-chloro-1-naphthyl)acetamide,
N-(4-methoxy-1-naphthyl)acetamide,
N-(4-hydroxy-1-naphthyl)-2-chloroacetamide,
N-(4-hydroxy-3-chloro-1-naphthyl)-2-chloroacetamide,
N-(4-hydroxy-1-naphthyl)-2,2-dichloroacetamide,
N-(4-hydroxy-5-chloro-1-naphthyl)-2-methoxyacetamide.
N-(4-hydroxy-5-chloro-1-naphthyl)-2-aminoacetamide,
N-(4-hydroxy-3-chloro-1-naphthyl)-2-aminoacetamide, and
N-(4-hydroxy-3-fluoro-1-naphthyl)acetamide.

The most preferred enhancers are p-hydroxycinnamic acid, 4'-hydroxyacetanilide and 3'-chloro-4'-hydroxyacetanilide.

Many of the enhancers of the Kricka et al and McClune patents are commercially available or obtained as described in those patents. The enhancers of structures (I), (II), (III) and (IV) can be prepared generally from known starting materials as follows:

In general, the halogenated compounds of Structures (I)–(IV) are prepared by halogenation of the known precursor anilide (for example, 4'-hydroxy- or alkoxyacetanilide, or an anilide of naphthalene) with a known halogenating agent such as sulfuryl chloride, sulfuryl bromide, or the free halogen in the presence of acid. Where the desired precursor is not available, an appropriately substituted phenol or naphthol can be nitrated by mild nitration using known techniques (for example, with nitric acid in a solvent such as glacial acetic acid) followed by hydrogenation, typically over platinum or paladium to produce the amine (see *J. Am. Chem. Soc.* 49, 1093, 1927). The amine is then acylated, for example, by condensation with the desired acylating agent such as an anhydride (for example, acetic anhydride) or an acid chloride such as acrylic acid chloride, to produce the anilide. Suitable acylation procedures are also described by Challis et al, *The Chemistry of Amides*, pp. 731–857, Intersciences Publishing, New York, 1970. If the selected starting materials do not already provide the requisite electron withdrawing groups, the resulting anilide can be conveniently halogenated as described above. Alternatively, the amine precursor to the anilide can be acylated with an acylating agent that provides the group at $R^2$ (for example, trichtoroacetic acid chloride or maleic anhydride), or the aromatic ring of the anilide can be alkylated, acylated or nitrated at the $R^4$ or $R^5$ (or both) positions using known techniques to provide the requisite electron withdrawing groups from $R^4$ and $R^5$.

It is important that the element also comprises a "micelle forming material" for the chemiluminescent composition. Such materials typically provide a non-ionic hydrophobic environment for the reaction of the chemiluminescent reagents with the product of reaction of the peroxidase with the oxidant. The micelle forming material has been found to reduce unwanted background signal.

Particularly useful micelle forming materials include, but are not limited to, cationic surfactants (such as cetyltrimethylammonium bromide, cetyltrimethylammonium chloride, dodecyltrimethylammonium chloride and didodecyldimethylammonium chloride), nonionic partially hydrogenated vegetable oils (such as those commercially available from Eastman Chemical Co. under the MYVACET tradename), an emulsion of olive oil and gum acacia, and others which would be apparent to one skilled in the art. Cetyltrimethylammonium bromide is preferred.

An emulsion of olive oil and gum acacia can be prepared by dissolving a mixture of gum acacia (30 g) and sodium benzoate (0.4 g) in distilled water (160 ml) with vigorous stirring. It is best to dissolve the benzoate first and then gradually add the gum acacia. Highly purified olive oil (30 ml) and the gum acacia solution (70 ml of 15 g/100 ml) are then transferred to a glass homogenizer jar and cooled at 4° C. for 30 minutes. After blending at low speed for 3 minutes, then at high speed for 10 minutes, the homogenate is again cooled for 30 minutes before a last homogenization for 10 minutes. The resulting emulsion is stored at 4° C. until it is used.

The emulsion of olive oil and gum acacia is generally used in a layer which also contains a latex polymer, coated at from about 1 to about 5 g/m². Such latices include any water-insoluble addition polymer which can be formed by emulsion polymerization techniques. Particularly useful latex polymers include, but are not limited to, poly(methyl acrylate-co-2-acrylamido-2-methylpropane sulfonic acid, sodium salt-co-2-acetoacetoxyethyl methacrylate), poly [acrylamide-co-vinylpyrrolidone-co-N-(3-acetoacetamidopropyl)methacrylamide] and similar polymers which would be readily apparent to one skilled in the art.

The oxidase in the element will depend upon the oxidase system used in the assay. Examples of useful oxidases include, but are not limited to, glucose oxidase, cholesterol oxidase, sarcosine oxidase, D-galactose oxidase, L-glycerol 3-phosphate oxidase, and others readily apparent to one skilled in the art. Glucose oxidase is preferred.

All of the reagents in one or more reagent layers are dispersed within one or more hydrophilic binders, which include, but are not limited to, gelatin and other colloidal materials (preferably, hardened with conventional hardeners), polyacrylamide, polyvinylpyrrolidone, copolymers of acrylamide and vinylpyrrolidone, mixtures of gelatin and such polymers, and others which would be readily apparent to one skilled in the art. Gelatin is most preferred. These binders are preferably hardened using conventional hardeners or by incorporating known crosslinking units (for example, active methylene groups) within the polymers.

Disposed over the reagent layer is a non-tacky, water-soluble or water-permeable cover layer. By "non-tacky" is meant that the element will not adhere to a gel plate or transblotting membrane and can be easily removed without damage to the gel plate or membrane. The layer is prepared from one or more water-soluble or water-permeable (for example, porous) materials which readily allow movement of fluids and water-soluble reagents used in the assay.

In one embodiment, the cover layer is prepared using conventional porous "spreading layers" as described in various publications, notably porous layers comprised of inorganic or organic particles, fibers or cellulosic materials, as described for example in U.S. Pat. No. 3,992,158 (Przybylowicz et al), U.S. Pat. No. 4,258,001 (Pierce et al), U.S. Pat. No. 4,292,272 (Kitazima et al) and U.S. Pat. No. 4,430,436 (Koyama et al). Particularly useful porous layers are what are known as "blush" spreading layers comprising titanium dioxide or barium sulfate in cellulose acetate and polyurethane binders. The amounts of materials needed to form such layers are well known in the art.

In preferred embodiments, the non-tacky nature of the cover layer is achieved by using a critical amount of one or more water-soluble or water-permeable, non-crosslinked film-forming polymers, such as vinylpyrrolidone polymers, acrylamide polymers and others readily apparent to one skilled in the art. Such polymers include polyvinylpyrrolidone, polyacrylamide, copolymers of vinylpyrrolidone with an acrylamide, polyisopropylacrylamide and other similar homopolymers and copolymers. Vinylpyrrolidone polymers, such as polyvinylpyrrolidone are more preferred. What are referred to in the art as "hydrogels" can also be used. Generally, the film-forming polymer (or mixtures thereof) is present in an amount of from about 0.2 to about 5.5 g/m$^2$, with from about 0.6 to about 2 g/m$^2$ being preferred, and about 0.6 g/m$^2$ being most preferred. Amounts greater than 5.5 g/m$^2$ may provide acceptable sensitivity, but the cover layer may become too tacky to remove easily from the gel plate or transblotting membrane.

Within a layer different from that containing the oxidase is a substrate for the oxidase. The particular substrate will depend upon the oxidase used, and could therefore be such materials as glucose, cholesterol, sarcosine, D-galactose, L-glycerol 3-phosphate and others readily apparent to one skilled in the art. Glucose is preferred in the practice of the invention.

Other layers can be interposed between the reagent layer and the support, or between the reagent layer and cover layer, including subbing layers and adhesive layers, as long as such layers do not inhibit the movement of reagents between the reagent and cover layers. A wash coat can be used to incorporate reagents if desired. There can be more than one reagent layer, although it is preferred to minimize the number of layers to aid diffusibility of the reagents. The various reagents used in the assay can be disposed in various layers, and several embodiments are illustrated in Examples 1 and 4–7 below. The element of Example 1 is preferred.

The element reagent layers are buffered with appropriate buffers to the same pH which is from about 7.5 to about 11. Preferably, the pH is from about 8 to about 9 with a pH of 8.5 being most preferred. Useful buffers for this purpose which do not interfere with the reactions necessary for the generation of the chemiluminescent signal include, but are not limited to, tris(hydroxymethyl)aminomethane and acid salts thereof, bicine, phosphate, sodium borate, 3-[1,1-dimethyl-2-hydroxyethyl]amino]-2-hydroxypropanesulfonic acid, 3-(N-morpholino)propanesulfonic acid and others readily apparent to one skilled in the art. Highly purified tris(hydroxymethyl) aminomethane and acid salts thereof are preferred.

Addenda that may be included within any of the layers of the element to improve coating or reagent mobility, or to prevent premature oxidation include nonionic surfactants, antioxidants, polymeric latices, coupler solvents and other materials readily apparent to one skilled in the coating art. The amounts of optional addenda in any layer of the element would be within the skill of the ordinary worker in the art.

The chemiluminescent compound is generally present in an amount of at least about 0.5 mg/m$^2$, with an amount in the range of from about 2 to about 200 mg/m$^2$ being preferred. The enhancer is generally present in an amount of at least about 1 mg/m$^2$, with an amount within the range of from about 2 to about 100 mg/m$^2$ being preferred. The buffers would be present in sufficient amounts to provide the desired buffering capacity both during element storage and in an assay. The micelle forming material is generally present in an amount of at least about 0.001 g/m$^2$, with from about 0.2 to about 2 g/m$^2$ being preferred. Any latex used with the olive oil and gum acacia may be present in an amount of from about 1 to about 5 g/m$^2$.

It is critical to high sensitivity in the assay that the amount of the oxidase in the element be in the range of from about 300 to about 40,000 I.U./m$^2$. Preferably, the oxidase is present at from about 1000 to about 10,000 I.U./m$^2$ with from about 2000 to about 6000 I.U./m$^2$ being most preferred. The amounts within these ranges will vary depending upon the oxidase used. It is also critical that the amount of oxidase substrate be at least about 1 g/m$^2$, with an amount of from about 1 to about 20 g/m$^2$ being preferred, from 5 to about 14 g/m$^2$ being more preferred and from about 8 to about 13 g/m$^2$ being most preferred for the longest and most intense signals. For a preferred embodiment, the ratio of glucose to glucose oxidase is about 2500 I.U./m$^2$:12.2 g/m$^2$. As used in this application, one I.U. represents the International Unit for enzyme activity and is defined as the amount of enzyme activity required to catalyze the conversion of 1 micromole of substrate per minute under standard pH and temperature conditions.

The test device of this invention comprises a dry, removable analytical element as described herein, and a photosensitive element adapted to receive and record chemiluminescent signal generated in the analytical element. The analytical element and photosensitive elements can be physically associated therewith, that is, in physical contact, or separated by transparent layers or supports which allow the chemiluminescent signal to be recorded by the photosensitive element. In one embodiment, the photosensitive element can be a photosensitive layer coated on the back side of the support of the analytical element. Alternatively, the analytical element and photosensitive element are not in physical contact, but in sufficient proximity so as to allow the signal to be recorded, for example, using a camera or other optical recording device.

The photosensitive element, in its simplest form, can be a self-supporting photosensitive layer comprising appropriate photosensitive reagents dispersed within a film or binder material. Suitable photosensitive reagents are well known and include black and white and color silver halide emulsions for both "instant" photography as well as non-instant photography, but the invention is not limited to those conventional reagents. The photosensitive element can also be a physical element such what are known as "charge coupled devices" which is in contact with or in the proximity of the chemiluminescent signal. The photosensitive reagents can also be disposed in one or more layers on a transparent support. The photosensitive element can be removable from the analytical element if it has been used as a temporary overlay to record the chemiluminescent signal. Optionally, the photosensitive element can also have a means for protecting it from ambient light, such as an opaque protective layer covering the surface not in physical association with the analytical element. The photosensitive element can be supplied in a cassette into which the analytical element is placed after exposure to the analytes, or the elements can be inserted together into the cassette during the assay.

A latent image is generally produced in the photosensitive element in response to the chemiluminescent signal, which latent image is developed using developing reagents appropriate for the particular photosensitive reagent used. The resulting image on the developed photosensitive element can be observed and evaluated as a means of determining the one or more analytes in the gel plate or transblotting membrane. The reagents and procedures for development of a wide variety of photosensitive elements are well known. One particularly useful photosensitive element is X-OMAT™ AR film which is available from Eastman Kodak Company.

In another embodiment, the chemiluminescent signal can be recorded on a photosensitive element containing phosphor screens. The recorded image can be transformed into digital signals which can then be evaluated or further recorded in a number of ways, including recording on magnetic tape, optical disks and other information recording media known to one skilled in the art. Alternatively, a latent image from the chemiluminescent signal can be produced or recorded electronically.

A method of this invention provides for the determination of one or more analytes by forming a temporary laminate of a gel plate or transblotting membrane and the analytical element of this invention.

Prior to this lamination, if the analytes are unlabeled, once they have been separated or immobilized in some fashion in the gel plates or transblotting membranes, they are labeled with peroxidase in a suitable fashion. If the analytes are proteins, typically peroxidase-labeled antibodies reactive with the protein analytes are applied to cause a complexation reaction with the analytes. If the analytes are nucleic acids, peroxidase-labeled probes which are complementary and hybridizable with the analytes are similarly used. If the analytes are already labeled with peroxidase (for example, the analytes are forms of the enzyme) or labeled directly or indirectly prior to separation or blotting techniques, the analytical element can be used immediately for detection. In some cases for the detection of proteins, unlabeled antibodies which will react specifically with the protein analytes are applied to the gel plate or transblotting membrane, followed by contact with a peroxidase-labeled anti-antibody. In still another embodiment, the analytes can be contacted with antibodies or probes labeled with streptavidin, which are then contacted with peroxidase-biotin conjugates.

Useful peroxidase-labeled antibodies and probes are readily available from a number of commercial sources, or can be prepared using known technology. For example, peroxidase labeling of antibodies can be achieved using the well known procedures of Yoshitake et al, *Eur. J. Biochem.*, 101, 395, 1979 and U.S. Pat. No. 5,106,732 (Kondo et al). The labeling of oligonucleotides for probes is also well known, for example as described in U.S. Pat. No. 4,962,029 (Levenson et al) and U.S. Pat. No. 5,082,780 (Warren III et al). The peroxidase-labeled reagents can be supplied in buffered solutions as is commonly known in the art. Alternatively, the peroxidase-labeled reagents are conjugates of a peroxidase and a specific binding moiety such as streptavidin or biotin.

In still another embodiment, the anti-antibodies mentioned above can be labeled with a conjugate of peroxidase and either a rhodamine, fluorescein or hydrazide to provide an increased, longer lasting or different chemiluminescent signal. Such conjugates can be readily prepared by modifying the rhodamine, fluorescein or hydrazide molecule appropriately so the peroxidase can be covalently reacted therewith. One skilled in the art would know how to do this and where to find the appropriate reagents.

By "peroxidase" in this application, we mean any peroxidative substance (enzymatic or otherwise) which catalyzes the oxidation of a substrate, such as a DPD (for example, luminol) or a similar compound to produce light. Microbial, fungal and plant peroxidases are preferred, with horseradish peroxidase being most preferred.

An oxidant is generally needed to produce the desired signal in the presence of a peroxidase and an enhancer as described above. Various useful oxidants are known, but perborate ion and hydrogen peroxide are preferred with hydrogen peroxide being most preferred. Hydrogen peroxide is typically generated upon the reaction of the oxidase with its substrate, but additional amounts of oxidant can be added to the system if desired.

Prior to labeling of analytes, the gel plate or transblotting membrane may be washed with an appropriate buffered salt solution to obtain desired moisture and pH on the surface. Then, if the analytes are nucleic acids, they are appropriately labeled as described above. Further washing may be carried out to remove unreacted materials prior to laminating the gel plate or transblotting membrane with the analytical element of this invention.

Where the analytes are proteins, other procedures can be used. For example, for Western blots, after washing and reaction of a first antibody specific to the analytes, a blocking solution may be applied to block unreacted sites. A highly useful blocking solution comprises a highly purified casein, or another non-immunoreactive protein. The labeled anti-antibody is then added, followed by another wash prior to contact with the analytical element. Southern blot procedures can also be used as one skilled in the art would readily appreciate.

The gel plate or transblotting membrane and the cover layer of the analytical element are placed together in a temporary laminate in such a manner that minimizes the number of air bubbles formed at the interface. The photosensitive element can be applied to the analytical element at this time if desired. Alternatively, the analytical element can be separated from the gel plate or transblotting membrane prior to recording the signal with the photosensitive element.

There is insufficient migration of reagents (such as oxidant and enhancer) between the gel plate or transblotting membrane and the analytical element unless moisture is present. The gel plate or transblotting membrane is usually wetted prior to laminating so that reagent diffusion and reaction of the peroxidase with the reagents readily occurs. Wetting can be advantageously accomplished with a buffered salt solution containing any of a number of buffers, such as tris(hydroxymethyl)-aminomethane, and an inorganic salt, such as sodium chloride.

The laminate is kept together for time sufficient to allow reaction of the peroxidase and reagents in the analytical element to provide the desired light signal. This time will vary depending upon the concentration of the analyte and the amounts of reagents in the analytical element. The optimum time may require some routine experimentation. Generally, the reaction is carried out at from about 5° to about 37° C., with a temperature of from about 20° to about 25° C. being preferred.

The analytical element of this invention can be supplied as part of a test kit, along with one or more other separately packaged components useful in using the analytical element of this invention in any of the assay embodiments. Such components include, but are not limited to a buffered salt solution for gel plates or transblotting membranes, a blocking solution containing non-immunoreactive blocking proteins such as highly purified casein, peroxidase-labeled specific binding molecules (such as peroxidase-labeled antibodies or streptavidin), oligonucleotides labeled directly or indirectly with a peroxidase, gel plates, transblotting membranes, electrophoretic or electrofocusing reagents and buffers, photosensitive element, photosensitive element developers, instructions for use, and other materials readily apparent to one skilled in the art.

By "non-immunoreactive blocking" protein is meant a protein which is not specifically reactive with an antibody or antigenic material, and which can be used to "block" reactive sites on a membrane or gel plate which would normally bind to various reagents in the assay non-specifically. Use of the "blocking" solution reduces background in the assay.

Preferably, a kit of this invention includes one or more of the following components with the preferred two-layer analytical element of this invention:

i) a buffered salt solution comprising tris(hydroxymethyl) aminomethane and an inorganic salt (such as an alkali metal, alkaline earth metal or ammonium salt), ii) a buffered blocking solution comprising from about 0.5 to about 5 weight percent of a nonimmunoreactive protein (such as purified casein, bovine serum albumin or non-fat dried milk, with 3% preferred), iii) a peroxidase-labeled specific binding reagent (such as a conjugate of peroxidase and an antibody, streptavidin or biotin), iv) an oligonucleotide labeled directly or indirectly with a peroxidase, v) a transblotting membrane, vi) a gel plate, and vii) a photosensitive element.

The following examples are included to illustrate the practice of this invention, and are not meant to be limiting in any way. All percentages are by weight unless otherwise noted.

Materials and Methods for Examples:

Glucose oxidase (19,400 I.U./mg) from *Aspergillus niger*, Type II, was obtained from Sigma Chemical Company, with the activity stabilized by addition of potassium gluconate.

Peroxidase-labeled antibodies were obtained from Dako Corporation and Sigma Chemical Company.

FLAG™ peptide labeled antibodies specific to alkaline phosphatase were obtained from L&RP (Kodak, New Haven, Conn.).

Polyacrylamide electrophoretic gels and nitrocellulose membranes were obtained from various commercial sources.

Biotinylated anti-FLAG™ peptide antibodies were prepared using conventional procedures and reagents.

Streptavidin-horseradish peroxidase conjugate was obtained from Scripps Laboratories.

X-OMAT™ AR film was obtained from Eastman Kodak Company.

pFLAGMac plasmid was obtained from L&RP (Kodak, New Haven, Conn.).

Biotinylated hind III digested lambda DNA size markers were obtained from United States Biochemicals.

The biotinylated probe for the plasmid was prepared by incorporating biotinylated deoxyuridine triphosphate (from Enzo Biochemical) using a DNA polymerase obtained from *Thermus thermophilus*.

The $^{32}$P labeled probe for the plasmid was prepared by incorporating $^{32}$P deoxyuridine triphosphate (from Amersham International) using a DNA polymerase from *Thermus thermophilus*.

BIODYNE™ B microporous polyamide membranes were obtained from Pall Corp.

Tris(hydroxymethyl)aminomethane buffer was obtained from BIO-RAD Laboratories.

The remainder of the materials and reagents were obtained from Eastman Kodak Company or prepared using readily available reagents and known procedures.

EXAMPLE 1

Preparation of Two-Layer Analytical Element

A preferred analytical element of this invention was prepared in the following manner:

On a gelatin subbed poly(ethylene terephthalate) support was coated an aqueous formulation to provide dry coverages of the following: luminol (57 mg/m$^2$), p-hydroxycinnamic acid enhancer (24.6 mg/m$^2$), cetyl- trimethylammonium bromide (49 mg/m$^2$), glucose oxidase (2500 I.U./m$^2$), tris(hydroxymethyl)aminomethane buffer (0.16 g/m$^2$, pH 8.5) and hardened gelatin (5 g/m$^2$).

After drying the first layer, a second formulation in water was coated to provide the dry coverages of the following: glucose (12.19 g/m$^2$) and polyvinylpyrrolidone binder (0.627 g/m$^2$) and dried. The resulting element of the present invention was useful to detect multiple analytes as described below in Example 2.

EXAMPLE 2

Detection of Multiple Nucleic Acids

This example demonstrates the use of the analytical element described in Example 1 to detect multiple nucleic acids which have been separated using the conventional Southern blotting procedure.

In particular, this example demonstrates the detection of various concentrations of the plasmid pFlagMac. The probes used in the assay were biotinylated oligonucleotides which are complementary to a sequence of the plasmid to be detected.

A standard high melting agarose electrophoretic gel plate was loaded with different concentrations (100 pg, 1 ng and 10 ng) of the plasmid analyte together with the biotinylated size marker nucleic acids. The nucleic acids were separated in the gel plate by being subjected to a voltage different according to standard procedures.

A prewetted BIODYNE™ B membrane was laminated to the gel plate to transfer the separate nucleic acids to the membrane. The biotinylated probe was then applied to the membrane and hybridization was allowed to occur at 60°–65° C. with gentle agitation overnight. The membrane was then washed with a heated (60° C.) solution (2 ml/cm$^2$) of 2× SSPE containing sodium dodecyl sulfate (0.1%) for 15 minutes, followed by another wash of heated 0.5× SSPE containing sodium dodecyl sulfate (0.1%) for 15 minutes.

After a quick wash of the membrane with "TBS" buffer (pH 7.5) containing tris(hydroxymethyl)aminomethane (100 mmolar) and sodium chloride (150 mmolar), a blocking solution (0.5 ml/cm$^2$) containing highly purified casein (0.5%) was applied to the membrane for 30 minutes at 42° C. with gentle agitation. The membrane was washed again with "TBS".

The streptavidin-horseradish peroxidase conjugate in "TBS" (diluted 1:5000, 0.25 ml/cm$^2$) was applied to the membrane and incubated at room temperature for 30 minutes.

The membrane was then washed three times (2 ml/cm$^2$) with "TBS" containing TRITON™ X-100 nonionic surfactant (1%) at room temperature for 5 minutes each. A final wash with "TBS" (pH 8.5) was carried out similarly just before lamination with the analytical element of Example 1.

The wetted membrane was then laminated to the element of Example 1 and placed in a conventional film cassette from which ambient light could be excluded. X-OMAT™ AR film was then placed on the support side of the analytical element, the cassette closed and exposure allowed to proceed for about 1 hour. The developed image on the film from the chemiluminescent signal was evaluated and found to clearly show the presence of the labeled nucleic acid analytes.

Comparison:

A similar experiment was carried out using a P$^{32}$-labeled probe (200 bases) for the plasmid analyte except that the film was laminated directly to the membrane after analyte separation. In order to obtain acceptable sensitivity, the photosensitive film had to be exposed to the resulting radioactive signal for at least 24 hours.

EXAMPLE 3

Detection of Multiple Proteins

This example demonstrates the use of the analytical element described in Example 1 to detect multiple proteins which have been separated using the conventional Western blotting procedure.

The FLAG™ peptide (available from Immunex Corp. and Eastman Kodak Company Laboratory & Research Products Division) is a commercially available protein tag useful to facilitate detection or affinity purification of proteins. The FLAG™ peptide can be introduced into a protein by conventional molecular cloning techniques.

In this example, four different proteins were tagged with the FLAG™ peptide, including alkaline phosphatase which was tagged in three different locations of the molecule. Samples of the tagged proteins were isolated from the expressing cell lines and electrophoretically separated on a conventional polyacrylamide gel plate using conventional procedures and buffers. The gel plate was then contacted with a conventional nitrocellulose membrane to transfer the separated proteins to the membrane.

The membrane was then contacted with a blocking solution containing 5% (weight) of highly purified casein for 1 hour at 37° C. After rinsing the membrane with a buffered solution ("TBS", pH 7.5) containing tris(hydroxymethyl) aminomethane (100 molar) and sodium chloride (150 mmolar), it was then incubated with a conventional biotinylated anti-FLAG™ peptide antibody (10 μg/ml) in "TBS" buffer (pH 7.8) for 30 minutes at room temperature. Following several washes with "TBS" buffer, the membrane was then incubated with a conventional streptavidin-horseradish peroxidase conjugate (0.3 μg/ml) for 30 minutes at 22° C. Two additional washes were then carried out using "TBS" buffer (pH 7.8 and then pH 8.5).

The moist membrane was then placed in contact with the analytical element described in Example 1, and the resulting laminate was placed in a cassette which could be secured from ambient light. A photographic element (X-OMAT™ AR film from Eastman Kodak Company) was then placed on the transparent support side of the analytical element, and the cassette was closed. The resulting chemiluminescent signal was recorded on the film over the next 30 minutes and when developed, it clearly showed the separated tagged proteins.

EXAMPLE 4

Two-Layer Analytical Element with Porous Cover Layer

This example shows a two-layer analytical element of this invention which has a porous spreading layer as the cover layer.

On a gelatin subbed poly(ethylene terephthalate) support was coated an aqueous formulation to provide dry coverages of glucose oxidase (20,000 I.U./m$^2$) in polyvinylpyrrolidone (0.63 g/m$^2$).

After drying the first layer, a second formulation was coated to provide a cover layer having dry coverages of the following: barium sulfate (94.8 g/m$^2$), cetyltrimethylammonium bromide (10 mg/m$^2$) and cellulose acetate binder (8.5 g/m$^2$). Once this layer was dried, the following were applied in an aqueous washing coating to give the noted dry coverages: luminol (57 mg/m$^2$), tris(hydroxymethyl) aminomethane buffer (0.16 g/m$^2$, pH 8.5), glucose (12.2 g/m$^2$), 4'-hydroxyacetanilide enhancer (36.7 mg/m$^2$) and sodium chloride (0.6 g/m$^2$).

EXAMPLE 5

Alternative Element with Porous Cover Layer

This element is like that described in Example 4 except that the cover layer was prepared to have dry coverages of titanium dioxide (57.8 g/m$^2$) instead of barium sulfate, cetyltrimethylammonium bromide (10 mg/m$^2$) and cellulose acetate binder (7.7 g/m$^2$).

EXAMPLE 6

Three-Layer Analytical Element

This example shows a three-layer analytical element of this invention which can be used to detect multiple analytes according to the teaching herein.

On a gelatin subbed poly(ethylene terephthalate) support was coated an aqueous formulation to provide dry coverages of the following: glucose oxidase (2500 I.U./m$^2$) in hardened gelatin (5.5 g/m$^2$).

After drying, a second reagent layer was coated using an aqueous formulation of p-hydroxycinnamic acid enhancer (24.6 mg/m$^2$), cetyltrimethylammonium bromide (49 mg/m$^2$), tris(hydroxymethyl)aminomethane buffer (0.16 g/m$^2$, pH 8.5) and hardened gelatin (5 g/m$^2$).

After drying the second layer, a third formulation in ethanol was coated to provide the dry coverages of the following: glucose (12.2 g/m$^2$) and polyvinylpyrrolidone binder (0.63 g/m$^2$) and dried.

EXAMPLE 7

Still Another Two-Layer Element

This example shows still another two-layer analytical element of this invention which is different than the elements described in Examples 1, 4 and 5.

On a gelatin subbed poly(ethylene terephthalate) support was coated an aqueous formulation to provide dry coverages of the following: p-hydroxycinnamic acid enhancer (24.6 mg/m$^2$), cetyltrimethylammonium bromide (49 mg/m$^2$), luminol (57 mg/m$^2$), glucose (12.2 g/m$^2$), tris (hydroxymethyl)aminomethane buffer (0.16 g/m$^2$, pH 8.5) and hardened gelatin (5 g/m$^2$).

After drying the first layer, a second formulation in water was coated and quickly dried to provide the dry coverages of the following: glucose oxidase (2500 I.U./m$^2$) and polyvinyl pyrrolidone binder (0.63 g/m$^2$).

All of the elements described in Examples 4–7 were successfully used to detect peroxidase-labeled analytes in either transblotting membranes or gel plates using reagents and procedures similar to those described in Examples 2 and 3 above.

The invention has been described in detail with particular reference to preferred embodiments thereof, but it will be understood that variations and modifications can be effected within the spirit and scope of the invention.

We claim:

1. A test kit for the determination of one or more analytes comprising:

21 a) a dry, removable analytical element for producing a chemiluminescent signal in response to the catalytic action of a peroxidase, said element comprising a transparent, nonporous support having disposed thereon, in order:

one or more reagent layers buffered to a pH of from about 7.5 to about 11 and containing one or more hydrophilic binders, and a non-tacky, water-soluble or water-permeable cover layer comprising from about 0.6 to about 2 g/m² of polyvinylpyrrolidone the element further comprising:

(a) a chemiluminescent composition that produces chemiluminescence in the presence of peroxidase, (b) an enhancer for said chemiluminescent composition, (c) a micelle forming material for said chemiluminescent composition, (d) from about 300 to about 40,000 I.U./m² of an oxidase, and (e) at least about 1 g/m² of a substrate for said oxidase, said components (a)–(e) being located in any of said layers provided that said oxidase and said oxidase substrate are in separate layers, and b) one or more separately packaged components selected from the group consisting of:

i) a buffered salt solution comprising tris (hydroxymethyl)aminomethane and an inorganic salt, ii) a buffered blocking solution comprising from about 0.5 to about 5 weight % of casein, iii) a peroxidase-labeled specific binding reagent, iv) an oligonucleotide labeled directly or indirectly with a peroxidase, v) a transblotting membrane, vi) a gel plate, and vii) a photosensitive element.

2. The kit of claim 1 wherein said dry, removable element comprises a transparent, nonporous support having disposed thereon, in order:

a reagent layer comprising a chemiluminescent composition, an enhancer for said chemiluminescent composition, a micelle forming material for said chemiluminescent composition, and from about 300 to about 40,000 I.U./m² of an oxidase, all disposed in a hydrophilic binder, and a non-tacky, water-soluble or water-permeable cover layer comprising from about 1 to about 20 g/m² of a substrate for said oxidase dispersed in said polyvinylpyrrolidone.

3. The kit of claim 2 wherein said cover layer comprises from about 5 to about 14 g/m² of said substrate dispersed in said vinylpyrrolidone.

4. The kit of claim 1 wherein said chemiluminescent composition, said enhancer and said micelle forming material are in the first reagent layer of said analytical element, located adjacent to said cover layer, said oxidase substrate is in said cover layer, and said oxidase is in a second reagent layer located between said first and reagent layer and said support.

5. The kit of claim 1 wherein said enhancer, said oxidase and said micelle forming material are in said first reagent layer, and said oxidase substrate and said chemiluminescent composition are in said cover layer of said analytical element.

6. The kit of claim 1 wherein wherein said chemiluminescent composition comprises a 2,3-dihydro-1,4-phthalazinedione,

22 said enhancer is p-iodophenol, 1,6-dibromonaphth-2-ol, 1-bromonaphth-2-ol, 6-hydroxybenzothiazole, 2,4-dichlorophenol, p-hydroxycinnamic acid, dehydroluciferin, N,N,N'N'-tetramethylbenzidine, p-bromophenol, p-chlorophenol, or a compound having any structure (I):

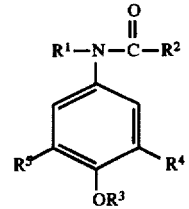

structure (II):

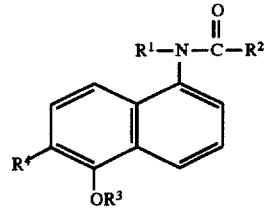

structure (III):

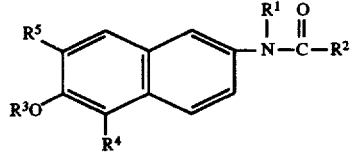

or structure (IV):

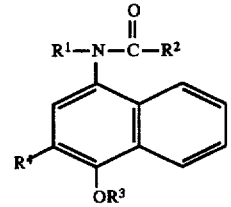

wherein $R^1$ is hydrogen or alkyl, $R^2$ is hydrogen, alkyl, alkoxyalkyl, hydroxyalkyl, aminoalkyl, haloalkyl or alkenyl, $R^3$ is hydrogen or alkyl, and $R^4$ and $R^5$ are independently hydrogen or an electron withdrawing group having a Hammett sigma value of at least about 0.01 and, said micelle forming material is an emulsion of olive oil and gum acacia, cetyltrimethylammonium bromide or cetyltrimethylammonium chloride.

7. The kit of claim 6 wherein said reagent layer is buffered to a pH of from about 8 to about 9, said oxidase is present in an amount of from about 1000 to about 10,000 I.U./m², said oxidase substrate is present in an amount of from about 5 to about 14 g/m², and said enhancer is present in an amount of from about 2 to about 100 mg/m².

8. The kit of claim 1 wherein said analytical element comprises a poly(ethylene terephthalate) support having disposed therein, in order:

a reagent layer comprising luminol, p-hydroxycinnamic acid, 4'-hydroxyacetanilide or 3'-chloro-4'-hydroxyacetanilide as an enhancer for luminol, cetyltrimethylammonium bromide and from about 2000 to about 6000 I.U./m² of glucose oxidase, all disposed in hardened gelatin, and a non-tacky, water-soluble or water-permeable cover layer comprising from about 8 to about 13 g/m² of glucose dispersed in about 0.6 g/m² of polyvinylpyrrolidone.

9. The kit of claim 1 wherein said photosensitive element is adapted to receive a chemiluminescent signal generated in said analytical element, said photosensitive element being physically associated with said analytical element.

10. The kit of claim 9 wherein said photosensitive element comprises a black and white or color photographic silver halide emulsion.

11. The kit of claim 9 comprising a phoshor screen.

12. The kit of claim 1 wherein said peroxidase-labeled specific binding reagent is an anti-antibody labeled with peroxide.

13. The kit of claim 12 wherein said anti-antibodies are labeled with a conjugate of peroxidase and either a rhodamine, fluorescein or hydrazide.

14. The kit of claim 1 wherein said peroxidase-labeled specific binding reagent is a conjugate of peroxide and streptavidin or biotin.

* * * * *